United States Patent [19]
Chen et al.

[11] Patent Number: 6,123,944
[45] Date of Patent: Sep. 26, 2000

[54] ICARIIN PREPARATIONS

[75] Inventors: Ying Jie Chen, Shenyang, China;
Patrick C. Kung, Cambridge, Mass.

[73] Assignee: PhytoCeutica, Inc., New Haven, Conn.

[21] Appl. No.: 09/045,160

[22] Filed: Mar. 19, 1998

[51] Int. Cl.$^7$ .......................... A61K 31/35; A61K 35/78
[52] U.S. Cl. .................. 424/195.1; 514/456; 514/783; 549/403
[58] Field of Search .................. 424/484, 195.1; 514/456, 783; 549/403

[56] References Cited

PUBLICATIONS

Civitelli et al., "Ipriflavone Improves Bone Density and Biomechanical Properties of Adult Male Rat Bones", Calcif Tissue Int. (1995) 56:215–219.

Coxam et al., "Effects of Dihydrotestosterone Alone and Combined with Estrogen on Bone Mineral Density, Bone Growth, and Formation Rates in Ovariectomized Rats", (1996) 19(2):107–114.

Dempster et al., "Temporal Changes in Cancellous Bone Structure of Rats Immediately After Ovariectomy", Bone (1995) 16(1):157–161.

Marsili et al., "Comparison of a Liquid Solvent Extraction Technique and Supercritical Fluid Extraction for the Determination α and β–Carotene in Vegetables", Cromatogr. Sci. (1983) 31:422–428.

Wronski et al., "Time Course of Vertebral Osteopenia in Ovariectomized Rats", Bone (1989) 10:295–301.

Yamazaki et al., "Effect of Ipriflavone on Glucocorticoid–Induced Osteoporosis in Rats", Life Sciences, (1986) 38:951–958.

Yingjie et al., "Studies of the Biologically Active Constituents of Epimedium Koreanum Nakai", Process in Drug Development from Medicinal Plants, Proceeding of UNESCO Regional Symposium on Drug Development from Medicinal Plants, Oct. 25–17, 1996, Hangzhou, China, organized by Shanghai Institute of Materia Medica, et al., in cooperation with United Nations Educational, Scientific and Cultural Organization.

*Primary Examiner*—Edward J. Webman
*Attorney, Agent, or Firm*—F&R Richardson P.C.

[57] ABSTRACT

Icariin-containing preparations obtained from the aerial parts of a plant of the genus Epimedium, comprising about 15% to about 95% icariin by weight and about 5% to about 80% non-icariin flavones by weight. Also disclosed are methods of obtaining such preparations from an Epimedium plant.

6 Claims, No Drawings

ICARIIN PREPARATIONS

BACKGROUND OF THE INVENTION

Osteoporosis affects 25 million women and men in the United States and resulted in 500,000 vertebral crush fractures, more than 250,000 hip fractures, and 200,000 distal radius fractures annually. An effective way of treating and preventing osteoporosis involves employing antiresorptive agents such as estrogen, calcitonin, and bisphosphonates. These agents suffer, however, from limited efficacy or undesired side effects. For example, estrogen therapy, which leads to an increase bone density at the lumbar spine in women, also brings about undesirable side effects such as weight gain and breast tenderness. In addition, concerns of a higher risk of breast and endometrial cancer that associates with long term estrogen treatment has prompted researchers to search for other agents that carry less side effects.

Chinese discovered centuries ago that plants of the genus Epimedium can strengthen bone and connective tissues. The general effect has been attributed to flavones (e.g., icariin, epimedins, anhydroicaritin, and karmferol), a class of compounds that are found in extracts of Epimedium plants.

SUMMARY OF THE INVENTION

The present invention features icariin-containing preparations and methods of obtaining such preparations. Also within the scope of this invention are icariin-standardized compositions.

One aspect of this invention relates to an icariin-containing preparation obtained from the aerial parts of plants of the Epimedium genus. The preparation contains about 15% to about 95% icariin by weight (e.g., about 20% to about 40%, about 40% to about 85%, about 85% to about 95%, and about 95%) and about 5% to about 80% of non-icariin flavones by weight. Icariin can be present in these preparations as either a neutral compound or as an ionic salt (e.g., icariin anion can associate with various cations such as sodium, potassium, and ammonium, etc.). Each of the just-mentioned icariin-containing preparations can be combined with one or more excipients to form an icariin-standardized composition, such as a pharmaceutical composition or a dietary supplement. Two icariin-standardized compositions are deemed as identical as long as they have the same icariin content; the other components or their respective contents may or may not be the same.

Another aspect of this invention relates to a process of obtaining an icariin-containing preparation from the Epimedium plants. The process begins with immersing the aerial parts of such plants in water. The aerial parts can be crushed to facilitate the extraction. The water is then heated for a sufficiently long period of time (e.g., 1 to 2 hours) to extract flavones and the debris is removed afterwards to yield an aqueous icariin-containing extract. This extraction process can be repeated on the filtered debris to maximize the amount of flavones being extracted. The aqueous extract from the species Epimedium koreanum typically contains about 1%–2% icariin and about 3%–10% non-icariin flavones by weight; the contents of these compounds do vary somewhat among different species of the Epimedium plants.

The icariin content in the aqueous icariin-containing extract obtained from the above process can be enriched by loading on a column that is packed with a hydrophobic macroporous polymer. The polymer is first washed with a polar eluent to remove unbound compounds while icariin and other flavones are still adsorbed on the polymer. Flavones can be subsequently eluted from the polymer with a less polar eluent. This polymer is preferred to be a crosslinked polyaromatic material, and, more preferably, a crosslinked polystyrene. The solvent of the eluate can be removed to yield a dry product by the method described in Example 2 below or any analogous method. In general, the weight percentage of icariin in the dry product is about 20% to about 40% icariin, as determined by HPLC or other analogous methods. This chromatography procedure unexpectedly allows a preferential enrichment of icariin over other non-icariin flavones. See Example 2 for a typical composition of the eluent.

The icariin content can be further enriched by a second chromatography procedure. More specifically, the above-described process is loaded on another column that is packed with a solid support which interacts with icariin via dipole-dipole or ionic attraction. Some examples of such solid supports are Baker WP, BioRad Ag, Amberlite, silica gel, and polyamide. A polar solvent is first employed as the mobile eluent phase to remove unbound compounds. Icariin and other non-icariin flavones are then eluted from the support with a less polar solvent. Another icariin-containing dry product can be produced by removing the solvent. The weight percentage of icariin in the dry product is generally about 40% to about 85%. The performance of different solid supports vary somewhat; most solid supports produce products containing between about 40% to about 65% icariin (w/w), with silica gel solid support produces a product having a higher icariin content (about 65% to about 85% by weight). The icariin content of this dry product can still be further enriched by crystallization. The crystallizing process should be carried out in solvents suitable for human consumption, e.g., ethanol. The weight percentage of icariin normally increases to about 85%–95% after the first crystallization process. Recrystallizations afford an icariin-containing product of about 95% icariin and about 5% non-icariin flavones. By using the above-described three purification procedures, i.e., two chromatography procedures and a crystallization process, the icariin content, unexpectedly, is increased from about 1%–2% to about 85%–95%.

Yet another aspect of the invention relates to a process of obtaining an icariin-containing preparation by using the two above-mentioned chromatography procedures in reverse order. Briefly, the aqueous icariin-containing etract described above is loaded onto a column packed with a solid support that associates with icariin via dipole—dipole or ionic interaction. The icariin-containing product from the first column is further processed by another column packed with a hydrophobic macroporous polymer. The icariin-containing preparation can then be crystallized, which affords a product having a higher icariin content (about 85%–95% by weight).

Each of the above-mentioned dry icariin-containing products can be combined with one or more excipients to form an icariin-standardized composition, such as a pharmaceutical composition or a dietary supplement.

Other features and advantages of the present invention will be apparent from the following description of the preferred embodiments, and also from the appending claims.

DESCRIPTION OF THE PREFERRED EMBODIMENTS

Extraction and Purification

An aspect of this invention relates to a process of preparing an icariin-containing product from the plant of the genus Epimedium. The process begins with extraction of icariin and other non-icariin flavones from the aerial parts of such an Epimedium plant. Some species within this genus are *E. acuminatum, E. baicaliquizhounense, E. baojingenensis, E. brevicornum, E. clongatum, E. caotum, E. davidii, E. ecalcaratum, E. fargesii, E. glandolospilosum, E. haiyangense, E. hunanense, E. leptorrhizum, E. koreanum, E. platypetalum, E. pubesens, E. reticulatum, E. sagittatum, E. simplicifolium, E. sutchuenense, E. truncatum, E. wushanense,* and *E. zushanense.* The aerial parts of the plant are usually crushed, dried, and washed to remove sand and dirt before being immersed in water. The flavones are then extracted into the water, preferably distilled, by heating, e.g., at about 100° C. This procedure can be repeated for a number of times to ensure that maximum extraction is achieved. Debris of the plant are filtered afterwards, e.g., by using a filter paper pulp, to produce an aqueous icariin-containing solution, which contains flavones and other organic compounds such as flavone glycosides, polyphenol, lignanoids, and ionoids. The content of icariin is normally about one-fifth to one-fourth of that of the combined flavones in the extract. Vacuum can be used in the just-mentioned filtration to aid the filtration.

The aqueous icariin-containing extract thus obtained can be subjected to hydrophobic chromatography to enrich the icariin content. Note that this procedure can also be applied to enrich icariin content in icariin-containing solutions prepared by other methods. The packing material used in this chromatography is a hydrophobic macroporous polymer, e.g., BioBead SM, Diaion (HP-10, HP-20, HP-30, HP-40, and HP-50), D201, and Dowex. Preferably, it is a crosslinked polyaromatic polymer. More preferably, it is a crosslinked polystyrene. Prior to being packed into a column, undesired compounds on the polymer are washed off with an solvent, e.g., ethanol, which is subsequently replaced with distilled water.

After pouring the aqueous icariin-containing extract into the polymer-packed column for the adsorption of icariin onto the polymer via hydrophobic interaction, a mobile eluent phase is used to remove any unbound compounds. The polarity of this mobile eluent phase is somewhat lower than water to enable compounds not tightly adsorbed onto the polymer to be eluted off, but not so nonpolar as to disrupt the hydrophobic interaction between icariin and the polymer. A less polar eluent is then employed to release icariin from the polymer. The eluate or preparation thus obtained can be concentrated in a vacuum evaporator to yield a dry icariin-containing powder. The powder has about equal weight percentage of icariin and other non-icariin flavones. By this single chromatography procedure, icariin has been unexpectedly and preferentially enriched over other flavones. Further, the content of icariin is enriched by 10–40 folds. The polymer can be regenerated by washing with ethanol, which renders this chromatography process rather inexpensive.

The icariin-containing preparation obtained from the above-described hydrophobic chromatography can be further processed by a second chromatography. Solid supports used in this procedure interacts icariin and other non-icariin flavones by dipole—dipole or ionic attraction. Examples of such solid supports include Baker WP, BioRad Ag, Diaion (WA-10 and WA-11), Amberlite (IR-45 and IRC-50), polyamide, and silica gel. The icariin content of the products obtained vary somewhat from using different types of resins. The icariin-containing eluate from the hydrophobic chromatography in the last process can be concentrated to a reduced volume. Alternatively, its dried-down product can be redissolved in water prior to being loaded onto the solid support of the second chromatography.

Similar to the first chromatography, a polar first mobile eluent phase is used to remove the undesired compounds. Icariin is subsequently eluted from the solid support by using a less polar mobile eluent phase. The solvent of the eluate can be removed to yield a dry powder. The eluate, which contains mostly flavones at this point, has a higher icariin content over that of the combined non-icariin flavones. Crystallization can be carried out after the second chromatography to obtain a product having an even higher icariin content.

The solid supports are reusable after washing off the adsorbed compounds. Although other polar solvents, e.g., methanol, can also be used in the purification, ethanol or diluted ethanol is the most preferred solvent (as both an eluent and a crystallizing solvent).

Note that the order of the two above-described chromatography procedures can be reversed. That is, the extract from the Epimedium plants can be first processed by a column that is packed with a dipole-dipole or an ionic interacting solid support, followed by the hydrophobic chromatography.

Alternative method of purification, such as supercritical fluid extraction with liquid carbon dioxide under high pressure (R. Marsili and D. Callahan, J. Chromatogr. Sci. vol. 31, page 422, 1993) can also be efficiently used to obtain icariin-containing preparations from the Epimedium plants.

Biological Activities

An effective amount of an icariin-containing preparations obtained from the above-described procedures can be combined with one or more excipients to form an icariin-standardized composition (e.g., a pharmaceutical composition or a dietary supplement) for treating or preventing osteoporosis. An effective amount of such a composition is defined as the amount which, upon administration to a subject in need, increases bone strength and mineral density, e.g., bone calcium and phosphorus contents, or otherwise confers a therapeutic or prophylactic effect on the treated subject. The effective amount to be administered to a subject is typically based on body surface area, weight, and the condition of that subject. Body surface area may be approximately determined from height and weight of the subject. See, e.g., Scientific Tables, Geigy Pharmaceuticals, Ardley, N.Y., 1970, 537. An effective amount of an icariin-containing preparation used to practice the invention can range from about 1 mg/kg to about 500 mg/kg, more preferably from about 1 mg/kg to about 50 mg/kg. Effective doses will also vary, as recognized by those skilled in the art, dependent on route of administration, excipient usage, and the possibility of co-usage with other therapeutic treatments including use of other antiresorptive agents such as estrogen, calcitonin, and bisphosphonates.

The icariin-standardized composition can be administered orally, or via the parenteral route, including subcutaneously, intraperitoneally, intramuscularly and intravenously. Examples of dosage forms include aqueous solutions of the active agent, in a isotonic saline, 5% glucose or other well-known pharmaceutically acceptable excipients. Solubilizing agents such as cyclodextrins, or other solubilizing agents well-known to those familiar with the art, can be utilized as pharmaceutical excipients for delivery of the therapeutic compounds. Formulation of an icariin-containing dry powder can be done, e.g., by dissolving the powder in slightly alkaline saline solution and adding carboxymethylcellulose (1% final concentration) to the saline solution to increase the bioavailability of the agent. The icariin-containing preparations of this invention are very stable during storage and can easily be formulated to give rise to a capsule, a tablet, softgel, or used in transdermal and time release devices, etc. Capsules may comprise any well-known pharmaceutically or dietarily acceptable material such as gelatin or cellulose derivatives. Tablets may be formulated in accordance with the conventional procedure by compressing mixtures of an icariin-containing dry products with a solid carrier, or a lubricant. Examples of solid carriers include inorganic salts, starch and sugar bentonite.

Bone calcium and phosphorus contents, bone mineral density, or femur breakage force can be used as an index for evaluating the efficacy of a composition of this invention. This number can be obtained from, for example, female Wistar rats that are bilateral ovariectomized. More specifically, after several weeks, e.g., ten to twelve weeks, of administration of the composition being tested, femur bones of the rats are stripped and processed for measurements of the content of calcium and phosphorus by atomic adsorption spectroscopy (I. Yamazaki et al., Life Sci., vol. 38, 951, 1986). Bone mineral density on the distal part of femur bones can then be measured with a photon absorptiometer (V. Coxam et al Bone Vol. 19(2): 107, 1996; Wronski et al, Bone,10:295, 1989; D. W. Dempster et al, Bone Vol. 16, No. 1, 157, 1995). Femur breakage force can be measured according to Yamazaki et al. (I. Yamazaki et al., Life Sci., vol. 38, 951, 1986; R. Civitelli et al., Calcif. Tissue Int., vol. 56, 215, 1995). These numbers can be compared with data obtained from two control groups, i.e., sham-operated and bilateral ovariectomized rats, that are administered with placebos.

Various icariin-containing compositions have been tested. It has been found that icariin-containing compositions with icariin content as low as about 20%–40% by weight are still effective in treating osteoporosis. Indeed, the bone phosphorus and calcium contents, the bone mineral density, and the femur strength of treated ovariectomized subjects are increased significantly, as compared with control groups. Further, co-treatment of an icariin-containing composition and estrogen surprisingly affords better efficacy.

Without further elaboration, it is believed that one skilled in the art can, based on the description herein, utilize parts or the whole procedure to its full extent. The following specific examples are, therefore, to be construed as merely illustrative, and not limitative of the remainder of the disclosure in any way whatsoever. All publications recited above and in the examples are hereby incorporated by reference.

EXAMPLE 1

In an extractor, 50 kg of dried aerial parts of *E. koreanum* (from Shenyang, China) were crushed into fine pieces, washed with water to remove sand, and then immersed in distilled water (i.e., about 20 times the weight of the aerial parts of the Epimedium plant) for 1.5 hours. The water which contained the aerial parts was boiled for one hour to obtain an aqueous extract. After filtering and collecting the extract, the aerial parts were boiled again with the same amount of distilled water for one hour to yield a second extract solution. The aqueous extracts were combined, cooled for 12 hours, and then filtered with a filter paper pulp under vacuum to yield a filtrate. The icariin content in this filtrate was estimated (by HPLC) to be about 1% (w/w), whereas the weight percentage of the non-icariin flavones was about 4%. That is, the ratio of icariin versus non-icariin flavones in the extract was about 1:4.

EXAMPLE 2

In enameled or stainless steel tub, 30 kg of a reusable and hydrophobic macroporous packing material (D3520 crosslinked polystyrene, purchased form the Chemical Factory, Nankai University, China) was stirred and rinsed with 95% ethanol in water (v/v; 1.5 to 2.0 times the weight of polystyrene) for three to five times. This procedure removed unbound compounds. The rinsed packing material was mixed with 95% ethanol (1.5 times of the volume of polystyrene) to form a thin slurry. The thin slurry was then poured into a glass column of diameter 250 mm and height 2000 mm, which was previously filled with 95% ethanol (½ to ⅓ volume of the column). The excessive amount of ethanol was slowly drained from the column so that an uniform bed of packing material could be formed without holes, channels, or air bubbles. The polystyrene was washed with 95% ethanol five times the volume of the polystyrene with a flow rate of 0.5 to 1.0 volume of polystyrene per hour until white turbid matter was no longer observed. Lastly, the polystyrene was washed with distilled water to remove ethanol present in the column.

The filtrate (1,000 L) obtained from the above-described extraction was loaded onto the washed D3520 crosslinked polystyrene (see washing procedure described above) with a flow rate of 1 to 2 volumes of the polystyrene per hour, to enable icariin and other non-icariin flavones to adsorb on the polystyrene via hydrophobic interaction.

The polystyrene was first washed with 100 L of 20% ethanol in water (v/v) to remove unbound compounds. 100 L of 60% ethanol in water was then used to elute flavones from the polystyrene to yield an icariin-containing eluate. The volume of each mobile eluent phase used was about 5 to 6 times the volume of the polystyrene. The flow rate of the eluent was maintained at about 0.5 to 1.0 volume of the polystyrene per hour.

The icariin-containing eluate was concentrated in a vacuum evaporator at a temperature of 100° C. and a pressure of 600 mmHg, until the volume was reduced to ⅟15 to ⅟20 of the original volume. Under the same conditions (i.e., same temperature and pressure), the enriched eluate was further concentrated in a vacuum dryer for 24 hours to yield a dry icariin-containing powder (1.3 kg) that contained about a 1:1 ratio of icariin versus non-icariin flavones. The composition of the icariin-containing product analyzed by HPLC is shown below.

| | |
|---|---|
| Icariin | 27% by weight |
| Non-icariin flavones | 23% by weight |
| Polyphenol and its glycosides | 35% by weight |
| Other compounds | 10% by weight |
| Water | <1.5% by weight |
| Ash | <3% by weight |

Non-icariin flavones include epimedins, anhydroicaritin, kaemferol, epimedokoreanin, ginkgetin, bioketin, and caohuoside. Other compounds refer to non-flavone, include lignanoids, tanins, terpenoids, ionoids, phenylpropanoids, and phenanthrenoids.

The product thus obtained, which contains about 27% icariin and about 23% non-icariin flavones, was tested and found to be effective in increasing bone phosphorus and calcium contents, bone mineral density, and femur strength.

The polystyrene could be regenerated after the eluate was collected by washing with 95% ethanol to remove less polar compounds until the ethanol eluate was almost colorless, followed by further washing with distilled water to remove ethanol. The ethanol could also be recovered from the wash solution by distillation.

EXAMPLE 3

The icariin content in the eluate from the above-described chromatography was further enriched by ionic chromatography.

More specifically, the ethanol in the eluate from the polystyrene column was removed and the remaining solution was loaded on an Amberlite IRC 50 column with a flow rate of 1 to 2 volume of the Amberlite resin per hour. The column was then washed with water to remove unbound compounds. After the washing procedure, 40% (v/v) ethanol in water (i.e., about 5 to 6 times the volume of Amberlite) was added to the column for elution of icariin and other non-icariin flavones from Amberlite. The flow rate was maintained at 0.5 to 1.0 volume of Amberlite per hour. The solvent of the eluate was removed as described above to yield an icariin-containing (determined by HPLC to be about 55%) dry product.

This product was then redissolved in 70% ethanol with heating (about 20–50 mL of ethanol solution was used for every gram of icariin). Undissolved materials were filtered afterwards. Crystals were formed as the filtrate was left undisturbed. This procedure was done in 100% ethanol.

The crystalline product which contains about 95% icariin by weight and about 5% non-icariin flavones by weight as determined by HPLC, was tested and found to be effective in increasing bone phosphorus and calcium contents, bone mineral density, and femur strength.

EXAMPLE 4

The extraction of flavones from the aerial parts of the Epimedium plants and enrichment of icariin in the extract by a polystyrene column are as described in Examples 1 and 2. The ethanol-containing eluate from the polystyrene column was mixed with a reusable hydrogen-bond interacting resin (about 3 times the weight of the eluate). A polyamide resin (30–60 mesh; batch no. 940823, purchased from Shanghai Chemical Regents Company, Shanghai, China) was used in this example. The ethanol present in the mixture of eluate and resin was evaporated and the concentrated mixture was then poured into a glass chromatography column. The resin was first washed with water, then 10% (v/v) ethanol in water until the eluate was colorless, then icariin was eluted from the resin with 30% ethanol in water. The eluate, which contained about 60% icariin, was evaporated to dryness. A crystallization procedure was carried out as described in Example 3.

This product, which contains about 95% icariin by weight and about 5% non-icariin flavones by weight, was tested and found to be effective in increasing bone phosphorus and calcium contents, bone mineral density, and femur strength.

EXAMPLE 5

The extraction of flavones from the aerial parts of the Epimedium plants and purification of the extract by a polystyrene column are as described in Examples 1 and 2. 500 g icariin-containing dry powder from the polystyrene column was dissolved in 70% ethanol in water and mixed with 70 kg silica gel (200–300 mesh, Shanghai Chemical Reagent Company, China). After removing the ethanol present in the mixture of icariin and silica gel by evaporation, this mixture was then poured into a glass chromatography column. Icariin was eluted from the silica gel by using 35 L of an eluent containing ethyl acetate, acetone, and water (100:20:1). The icariin-containing eluate was concentrated to yield 100 g dry product, which contains about 80% icariin. Crystallization of icariin from the above-described dry product was then performed in 100% ethanol (in the ratio of about 1 g icariin-containing dry product to 15 mL of ethanol) and resulted in 80 g of icariin-containing product. Recrystallization of this just-mentioned product in ethanol afforded an icariin-containing product that contains about 95% icariin by weight and 5% non-icariin flavones by weight.

This product was tested and found to be effective in increasing bone phosphorus and calcium contents, bone mineral density, and femur strength.

OTHER EMBODIMENTS

From the above description, one skilled in the art can easily ascertain the essential characteristics of the present invention, and without departing from the spirit and the scope thereof, can make carious changes and modifications of the invention to adapt it to various usages and conditions. Thus, other embodiments are also within the claims.

What is claimed is:

1. An icariin-containing dry product prepared by the process comprising:

immersing the aerial parts of a plant of the genus Epimedium in water;

heating the water in which the aerial parts of the plant are immersed;

removing debris to obtain an aqueous icariin-containing solution;

loading the aqueous icariin-containing solution on a column packed with a hydrophobic macroporous polymer for adsorption of icariin onto the polymer;

washing the column with a first polar solvent as the mobile eluent phase to remove unbound compounds with icariin remained adsorbed onto the polymer;

eluting icariin from the polymer with a second polar solvent to obtain an icariin-containing eluate, the second polar solvent being less polar than the first polar solvent; and removing the solvent of the icariin-containing eluate to yield a dry product.

2. An icariin-containing dry product prepared by the process comprising:

immersing the aerial parts of a plant of the genus Epimedium in water;

heating the water in which the aerial parts of the plant are immersed;

removing debris to obtain an aqueous icariin-containing solution;

loading the aqueous icariin-containing solution on a column packed with a hydrophobic macroporous polymer for adsorption of icariin onto the polymer;

washing the column with a first polar solvent as the mobile eluent phase to remove unbound compounds with icariin remained adsorbed onto the polymer;

eluting icariin from the polymer with a second polar solvent to obtain an icariin-containing eluate, the second polar solvent being less polar than the first polar solvent;

loading the icariin-containing eluate on a second column packed with a solid support for adsorption of icariin onto the support via dipole—dipole or ionic interaction;

washing the column with a third polar solvent as the mobile eluent phase to remove unbound compounds with icariin remained adsorbed onto the support; and eluting icariin from the support with a fourth polar solvent to obtain an icariin-containing eluate, the fourth polar solvent being less polar than the third polar solvent; and removing the solvent of the icariin-containing eluate from the second column to yield a dry product.

3. An icariin-containing product prepared by the process comprising:

immersing the aerial parts of plant of the genus Epimedium in water;

heating the water in which the aerial parts of the plant are immersed;

removing debris to obtain an aqueous icariin-containing solution;

loading the aqueous icariin-containing solution on a column packed with a hydrophobic macroporous polymer for adsorption of icariin onto the polymer;

washing the column with a first polar solvent as the mobile eluent phase to remove unbound compounds with icariin remained adsorbed onto the polymer;

eluting icariin from the polymer with a second polar solvent to obtain an icariin-containing eluate, the second polar solvent being less polar than the first polar solvent;

loading the icariin-containing eluate on a second column packed with a solid support for adsorption of icariin onto the support via dipole—dipole or ionic interaction;

washing the column with a third polar solvent as the mobile eluent phase to remove unbound compounds with icariin remained adsorbed onto the support; and eluting icariin from the support with a fourth polar solvent to obtain an icariin-containing eluate, the fourth polar solvent being less polar than the third polar solvent;

removing the solvent of the icariin-containing eluate from the second column to yield a dry product; and redissolving and crystallizing the icariin-containing dry product to yield an icariin-containing preparation which contains about 95% icariin by weight.

4. An icariin-containing dry product prepared by the process comprising:

immersing the aerial parts of plant of the genus Epimedium in water;

heating the water in which the aerial parts of the plant are immersed;

removing debris to obtain an aqueous icariin-containing solution;

loading the aqueous icariin-containing solution on a column packed with a solid support for adsorption of icariin onto the support via dipole-dipole or ionic interaction;

washing the column with a first polar solvent as the mobile eluent phase to -remove unbound compounds with icariin remained adsorbed onto the support;

eluting icariin from the support with a second Polar solvent to obtain an icariin-containing eluate, the second polar solvent being less polar than the first polar solvent; and removing the solvent of the icariin-containing eluate to yield a dry product.

5. An icariin-containing dry product prepared by the process comprising:

immersing the aerial parts of plant of the genus Epimedium in water;

heating the water in which the aerial parts of the plant are immersed;

removing debris to obtain an aqueous icariin-containing solution;

loading the aqueous icariin-containing solution on a column packed with a solid support for adsorption of icariin onto the support via dipole—dipole or ionic-interaction;

washing the column with a first polar solvent as the mobile eluent phase to remove unbound compounds with icariin remained adsorbed onto the support;

eluting icariin from the support with a second polar solvent to obtain an icariin-containing eluate, the second polar solvent being less polar than the first polar solvent;

loading the icariin-containing eluate on a column packed with a hydrophobic macroporous polymer for adsorption of icariin onto the polymer;

washing the column with a third polar solvent as the mobile eluent phase to remove unbound compounds with icariin remained adsorbed onto the polymer;

eluting icariin from the polymer with a fourth polar solvent to obtain an icariin-containing eluate, the fourth polar solvent being less polar than the third polar solvent; and removing the solvent of the icariin-containing eluate to yield a dry product.

6. An icariin-containing product prepared by the process comprising:

immersing the aerial parts of plant of the genus Epimedium in water;

heating the water in which the aerial Parts of the plant are immersed;

removing debris to obtain an aqueous icariin-containing solution;

loading the aqueous icariin-containing solution on a column packed with a solid support for adsorption of icariin onto the support via dipole—dipole or ionic interaction;

washing with a first polar solvent as the mobile eluent phase to remove unbound compounds with icariin remained adsorbed onto the support;

eluting icariin from the support with a second polar solvent to obtain an icariin-containing eluate, the second polar solvent being less polar than the first polar solvent;

loading the icariin-containing eluate on a column packed with a hydrophobic macroporous polymer for adsorption of icariin onto the polymer;

washing the column with a third Polar solvent as the mobile eluent Phase to remove unbound compounds with icariin remained adsorbed onto the polymer;

eluting icariin from the polymer with a fourth polar solvent to obtain an icariin-containing eluate, the fourth polar solvent being less polar than the third polar solvent; and removing the solvent of the icariin-containing eluate to yield a dry product; and redissolving and crystallizing the icariin-containing dry product to yield an icariin-containing preparation which contains about 95% icariin by weight.

* * * * *